United States Patent [19]

Minton et al.

[11] 4,197,212

[45] Apr. 8, 1980

[54] GELLED NAIL POLISH REMOVER AND PROCESS OF MAKING THE SAME

[75] Inventors: Abraham Minton, Rego Park; James H. Baker, Jackson Heights, both of N.Y.; James Teng, St. Louis County, Mo.

[73] Assignee: Anheuser-Busch, Incorporated, St. Louis, Mo.

[21] Appl. No.: 900,493

[22] Filed: Apr. 27, 1978

Related U.S. Application Data

[63] Continuation of Ser. No. 376,126, Jul. 3, 1973, abandoned.

[51] Int. Cl.$^2$ .............................................. C11D 7/52
[52] U.S. Cl. ................................. 252/164; 106/187; 252/163; 252/165; 252/166; 252/167; 252/168; 252/DIG. 8; 424/61
[58] Field of Search ............... 252/163, 164, 165, 166, 252/167, 168, DIG. 8, 170; 202/316; 106/187; 424/61

[56] References Cited

U.S. PATENT DOCUMENTS

| | | | |
|---|---|---|---|
| 2,032,042 | 2/1936 | Bishop | 252/170 |
| 3,824,085 | 7/1964 | Teng et al. | 44/7 B |

OTHER PUBLICATIONS

"American Perfumer and Cosmetics", vol. 86, Oct. 1971, p. 34.

*Primary Examiner*—Mayer Weinblatt
*Attorney, Agent, or Firm*—Gravely, Lieder & Woodruff

[57] ABSTRACT

This application discloses a solvent based nail polish remover comprising 85.0 to 99.5% acetone or ethyl acetate solvent and 0.5 to 15% gelling agent, preferably hydroxypropyl cellulose acetate gelling agent. The gelled remover has a viscosity of 1,000 to 10,000 centipoise and possesses little odor due to the low rate of solvent evaporation when compared to acetone alone. The consistency of the gel allows it to be packaged in a collapsible tube to avoid breakage or spillage. The process includes the steps of adding the gelling agent to the acetone or ethyl acetate solvent after the addition of the other ingredients.

1 Claim, No Drawings

GELLED NAIL POLISH REMOVER AND PROCESS OF MAKING THE SAME

This is a continuation of application Ser. No. 376,126, filed July 3, 1976, abandoned.

BACKGROUND OF THE INVENTION

In the cosmetic field, it is desirable to have a nail polish remover that is easy to use and convenient, that is, one that can be easily spread on the nail and carried in a purse or suitcase without the danger of breaking or spilling, and which, when placed on the nail does not spread or run unduly. The nail polish remover should provide a proper foundation for nail polish without excessive drying of the nails while maintaining a glossy appearance. It is also desirable to reduce the unpleasant odor of nail polish removers and to avoid waste due to excessive application and spillage. Heretofore, no nail polish remover has been found which meets all of these requirements.

SUMMARY OF THE INVENTION

The present invention comprises a nail polish remover comprising about 85.0 to about 99.5% nail polish solvent and about 0.5 to about 15% gelling agent, said remover having a viscosity of about 1,000 to about 10,000 centipoise. The preferred solvent is acetone and the preferred gelling agent is hydroxypropyl cellulose acetate. The present invention further comprises a process by which the gelling agent is added to the acetone solvent after the addition of all other ingredients.

DETAILED DESCRIPTION

Many gelling agents can be used in this invention with conventional nail polish removers and are categorized as follows: (A) cellulose derivatives such as hydroxypropyl cellulose, cellulose acetate butyrate, and ethyl hydroxyethyl cellulose; (B) synthetic derivatives such as polystyrene, and methyl vinyl ether and maleic anhydride copolymers, and (C) inorganic materials such as colloidal silica, and Bentone clay, a complex of bentonite and various quaternary compounds made by the NL Corporation. The preferred gelling agent is an acetate ester of hydroxypropyl cellulose. The hydroxypropyl cellulose acetate is particularly useful as a gelling agent for organic solvents such as acetone or ethyl acetate commonly used as solvents in nail polish removers.

The preparation of the preferred gelling agent is described in co-pending application Ser. No. 222,660 of Teng et al which is assigned to the assignee of the present invention. The reactants include only acetic anhydride, pyridine and hyroxypropyl cellulose. The reactants in some situations can be dissolved in the material to be gelled and the gel forms in situ.

The hydroxypropyl cellulose ester to be used as the gelling agent in this invention can have a degree of molar substitution (M.S.) of about 3 to about 5.

The M.S. determines the number of moles of

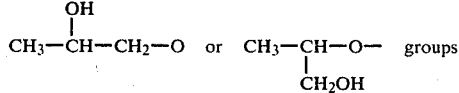

per anhydroglucose unit of the cellulose.

The esters of hydroxypropyl cellulose can have a degree of substitution (D.S.) of 0 to 3. The theoretical maximum is a D.S. of 3. With the acetate, the degree of substitution for effective compounds is about 1.0 to about 2.4.

There are three hydroxyl groups in each anhydroglucose unit in the cellulose molecular. D.S. is the average number of hydroxyl groups substituted in the cellulose per anhydroglucose unit. For the hydroxyalkyl derivatives of cellulose, the M.S. is generally greater than the D.S. The reason for this is that the hydroxyalkyl group is capable of homopolymerization.

The solvent to be used in the nail polish remover can be acetone or ethyl acetate. Other ketones besides acetone and other esters beside ethyl acetate will dissolve nail polish. However, these other solvents evaporate too slowly or have too much of an odor. From about 85% to about 99.5% solvent by weight is used. Acetone is preferred because it is recognized as the most efficient, least persistent in odor, and most economical to use. When acetone is the solvent from about 95 to about 99.5% by weight solvent is used in the composition.

The color tint is introduced into the nail polish remover by any commercially available grind. From about 0.05 to about 0.2% by weight coloring is used in the composition.

The pearlescent appearance is obtained by the use of Timica, a specially treated mica manufactured by the Mearl Corporation or by means of bismuth oxychloride pearly pigment (70% grind in castor oil), produced by Rona Pearl Corporation. From about 0.2 to about 0.5% by weight pearlescent material is used in the composition.

Pigmentation is accomplished by means of an oil-dispersible titanium dioxide grind in castor oil (40% titanium dioxide). From about 0.2 to about 0.8% by weight pigment is used in the composition.

The amount of preferred gelling agent, hydroxypropyl cellulose acetate, used in this invention is about 0.5 to about 5.0% by weight.

The viscosity of the gelled nail polish remover ranges from about 1000 cps to about 10,000 cps measured by a Brookfield viscometer. The specific gravity of the composition ranges from 0.79 to about 0.92.

EXAMPLE NO. 1

The preferred embodiment of the present invention is formulated as follows:

| | |
|---|---|
| Acetone | 98.0% by weight |
| Durlin Red Grind #50 | 0.1% by weight |
| Rona Non-Lead Pearl NLY-L-2X (70% in castor oil) | 0.4% by weight |
| Gelling Agent (hydroxypropyl cellulose acetate with M.S. of 4.0 and D.S. of 1.3) | 1.5% by weight |

In order to obtain a fine suspension of pigments, the addition of the grinds to the acetone must be made before the gelling agent is added. Should the grinds be added after the gelling agent is incorporated, they will not disperse.

This process requires a covered mixer with an explosion-proof motor connected to a shaft to which is attached the appropriate propellers. The cover is to prevent the evaporation of ingredients while stirring and storing.

The acetone is added to the mixer and stirred at medium speed. The pigment grinds are added and thoroughly dispersed. The hydroxypropyl gelling agent is added to the vortex. The vortex may disappear after approximately 5 minutes; if so, the stirring should be increased. It requires about 15 to 20 minutes for the hydroxypropyl cellulose acetate gelling agent to completely dissolve. Upon dissolution of the gelling agent the nail polish remover has a viscosity of about 2000 cps as measured by Brookfield RTV viscometer with #6 spindle at 20 rpm and 25° C., and a specific gravity of 0.79 to 0.82, substantially that of the solvent being gelled. The gel which is formed has a long shelf life, develops no syneresis, and is stable to temperature changes and vibrational influences. Gels can usually be formed at concentrations below 1.5% gelling agent. The thickened nail polish remover exhibits thixotropic or pseudo-plastic properties at low concentrations.

The following examples show various formulae that can be used in making the composition of this invention according to the process described in Example 1.

EXAMPLE NO. 2

Ethyl acetate as solvent in finger nail polish remover

| | |
|---|---|
| Ethyl acetate | 97.8% by weight |
| Titanium dioxide (40% in castor oil) | 0.6% by weight |
| Rona Non-Lead Pearl NLY-L-2X (70% in castor oil) | 0.4% by weight |
| Gelling Agent (hydroxypropyl cellulose acetate of M.S. of 4.0 and D.S. of 1.2. | 1.2% by weight |

The same mixing procedure is observed as in Example 1 and the resulting gelled nail polish remover has a viscosity of about 800 cps as measured by Brookfield RTV viscometer #6 spindle at 20 rpm at 25° C.

EXAMPLE NO. 3

Ethyl hydroxyethyl cellulose as a gelling agent

The gelling agent in Example 1 may be replaced by another cellulose derivative such as ethyl hydroxyethyl cellulose but the necessary concentration is much higher.

| | |
|---|---|
| Acetone | 95% by weight |
| Durlin Red Grind #50 | 0.1% by weight |
| Rona Non-Lead Pearl NLY-L-2X (70% in castor oil) | 0.4% by weight |
| Ethyl hydroxyethyl cellulose (Sold under trademark EHEC by Hercules, Inc.) | 4.5% by weight |

The nail polish remover made from this formulation is made according to the procedure of Example 1.

EXAMPLE NO. 4

Synthetic polymer as a gelling agent

The gelling agent in Example 1 may be replaced by a synthetic polymer, such as a vinyl ether copolymer.

| | |
|---|---|
| Acetone | 93.5% by weight |
| Durlin Red Grind #50 | 0.1% by weight |
| Rona Non-Lead Pearl NLY-L-2X (70% in castor oil) | 0.4% by weight |
| Polymer (methyl vinyl ether/maleic anhydride) | 6.0% by weight |

The foregoing formula is made utilizing the procedure followed in Example 1.

EXAMPLE NO. 5

Colloidal silica as a gelling agent

The gelling agent in Example 1 may be replaced by colloidal silica. In such case, a high speed homogenizer is used in the place of a covered mixer to disperse the silica in order to achieve a stable gel.

| | |
|---|---|
| Acetone | 84.5% by weight |
| Durlin Red Grind #50 | 0.1% by weight |
| Rona Non-Lead Pearl NLY-L-2X (70% in castor oil) | 0.4% by weight |
| Colloidal Silica | 15% by weight |

The composition of this invention can be packaged in a collapsible tube which is convenient to carry. The orifice of the tube is shaped to control the flow of the gel emitted onto the nail. The gelled remover is sufficiently thick so that it does not run or spread by itself after being applied to a nail.

The rate of evaporation of the solvent is subdued because it is in the gel form and enclosed within a tube. This means less odor and whatever odor present can be easily masked with perfume.

The composition is then ready to be spread over the nail or cuticle with a cotton pledget to remove the polish. After removal of the polish, a small quantity of the hydroxypropyl cellulose gelled polish remover remains on the nail in the form of a very thin, glossy film. Hydroxypropyl cellulose is compatible with the nitrocellulose present in all nail polishes and this residual film also acts as an anchor coat or base coat for the next application of polish and therefore does not leave the nail excessively dry.

Thus, it is seen that the present invention achieves all the objects and advantages sought therefor. This invention is intended to cover all changes and modifications of the example of the invention herein chosen for purposes of the disclosure which do not constitute departures from the spirit and scope of the invention.

What is claimed is:

1. A nail polish remover composition for use in removing finger nail polish from human nails comprising:
   a. from about 0.5 to about 15% by weight of a hydroxypropyl cellulose acetate gelling agent having a M.S. of about 3 to 5 and a D.S. of about 1.0 to about 2.4,
   b. from about 85 to about 99.5% by weight nail polish solvent selected from a ground consisting of ethyl acetate and acetone, c. a small but effective amount of pigmentation to provide the desired color and sheen to the composition,
d. said remover composition having a viscosity of about 1000 to about 10,000 centipoise as measured by a Brookfield viscometer at 20 rpm #6 spindle at 25° C., and a specific gravity of about 0.79 to about 0.92, and
e. said remover composition leaving a film adhering to the nail after evaporation of the solvent, which film has a sheen and provides a base compatible with a subsequent nail polish coating.

* * * * *